United States Patent
Parng et al.

(10) Patent No.: US 8,703,070 B1
(45) Date of Patent: Apr. 22, 2014

(54) APPARATUS FOR IMMUNOASSAY

(71) Applicant: Industrial Technology Research Institute, Hsin-Chu (TW)

(72) Inventors: Shaw-Hwa Parng, Kaohsiung (TW); Chih-Wen Yang, Taoyuan County (TW); Yu-Yin Tsai, Kaohsiung (TW); Yi-Chau Huang, Kaohsiung (TW)

(73) Assignee: Industrial Technology Research Institute, Hsin-Chu (TW)

( * ) Notice: Subject to any disclaimer, the term of this patent is extended or adjusted under 35 U.S.C. 154(b) by 0 days.

(21) Appl. No.: 13/667,341

(22) Filed: Nov. 2, 2012

(30) Foreign Application Priority Data

Apr. 24, 2012 (TW) .............................. 101114541 A
May 30, 2012 (TW) .............................. 101119292 A

(51) Int. Cl.
*B01L 3/00* (2006.01)
*G01N 21/64* (2006.01)

(52) U.S. Cl.
CPC ....... *B01L 3/5025* (2013.01); *B01L 2300/0803* (2013.01); *B01L 3/5027* (2013.01); *B01L 3/502738* (2013.01); *G01N 21/6452* (2013.01); *Y10S 436/805* (2013.01); *Y10S 436/809* (2013.01); *Y10S 435/808* (2013.01)
USPC ............ 422/503; 422/52; 422/72; 422/82.05; 422/82.06; 422/82.07; 422/82.08; 422/82.09; 422/82.11; 422/407; 422/500; 422/501; 422/502; 422/504; 422/930; 436/52; 436/53; 436/164; 436/165; 436/172; 436/518; 436/524; 436/525; 436/526; 436/805; 436/809; 435/164; 435/165; 435/283.1; 435/287.1; 435/287.2; 435/288.7; 435/808; 435/4; 435/5; 435/7.2; 435/7.9

(58) Field of Classification Search
CPC ................ B01L 3/5025; B01L 5/5027; B01L 3/502738; B01L 2300/0803; G01N 21/6452
USPC ......... 422/52, 72, 82.05, 82.06, 82.07, 82.08, 422/82.09, 82.11, 407, 500, 501, 502, 503, 422/504, 930; 436/52, 53, 164, 165, 172, 436/174, 518, 524, 525, 526, 805, 809; 435/164, 165, 283.1, 287.1, 287.2, 435/288.7, 808, 4, 5, 7.2, 7.9
See application file for complete search history.

(56) References Cited

U.S. PATENT DOCUMENTS 5,061,381 A  10/1991 Burd
5,160,702 A  11/1992 Kopf-Sill et al.
(Continued)

FOREIGN PATENT DOCUMENTS

CN     102170971    8/2011
TW      517154      1/2003
(Continued)

OTHER PUBLICATIONS

Cho et, al., "Lab-on-a-disc for simultaneous analysis of blood chemistry and immunoassay", Oct. 12-16, 2008, pp. 462-464, Twelfth International Conference on Miniaturized Systems for Chemistry and Life Sciences, San Diego, California, USA.

(Continued)

*Primary Examiner* — Dennis M White
(74) *Attorney, Agent, or Firm* — WPAT, PC; Justin King

(57) ABSTRACT

Apparatus for immunoassay includes: a cartridge, including at least one test unit; a pin-film assembly, having a second sealing film, a plurality of pierce mechanisms, and a first actuation unit; a plurality of magnetic particles; at least one first magnetic unit; and at least one second magnetic unit. The test unit includes a plurality of fluid chambers, a plurality of pin chambers, a microchannel structure, a buffer chamber, a detection chamber and a waste chamber. The first actuation unit drives the pierce mechanisms to enable a working fluid to flow into the detection chamber storing the magnetic particles. As the second magnetic unit has a magnetic force larger than that of the first magnetic unit and can move reciprocatingly between a third position and a fourth position, the magnetic particles are driven to move reciprocatingly inside the detection chamber, thereby fully mixing the magnetic particles with the working fluid.

17 Claims, 10 Drawing Sheets

(56) References Cited

U.S. PATENT DOCUMENTS

| | | |
|---|---|---|
| 5,173,193 A | 12/1992 | Schembri |
| 5,186,844 A | 2/1993 | Burd et al. |
| 5,275,016 A | 1/1994 | Chatterjee et al. |
| 5,304,348 A | 4/1994 | Burd et al. |
| 5,409,665 A | 4/1995 | Burd |
| 5,413,732 A | 5/1995 | Buhl et al. |
| 5,472,603 A | 12/1995 | Schembri |
| 5,478,750 A | 12/1995 | Bernstein et al. |
| 5,590,052 A | 12/1996 | Kopf-Sill et al. |
| 5,591,643 A | 1/1997 | Schembri |
| 6,454,970 B1 | 9/2002 | Ohman et al. |
| 6,620,478 B1 | 9/2003 | Ohman |
| 6,632,656 B1 | 10/2003 | Thomas et al. |
| 6,811,736 B1 | 11/2004 | Ohman et al. |
| 6,818,415 B2 | 11/2004 | Chiang |
| 6,878,255 B1 | 4/2005 | Wang et al. |
| 6,878,555 B2 | 4/2005 | Andersson et al. |
| 6,884,395 B2 | 4/2005 | Tooke et al. |
| 7,169,360 B2 | 1/2007 | Ågren et al. |
| 7,177,767 B2 | 2/2007 | Ostoich et al. |
| 7,189,368 B2 | 3/2007 | Andersson et al. |
| 7,238,255 B2 | 7/2007 | Derand et al. |
| 7,261,858 B2 | 8/2007 | Ågren et al. |
| 7,261,859 B2 | 8/2007 | Andersson et al. |
| 7,273,590 B2 | 9/2007 | Yao et al. |
| 7,429,354 B2 | 9/2008 | Andersson et al. |
| 7,553,393 B2 | 6/2009 | Derand et al. |
| 7,708,881 B2 | 5/2010 | Yu |
| 7,776,267 B2 | 8/2010 | Lee et al. |
| 7,790,110 B2 | 9/2010 | Cho et al. |
| 7,819,138 B2 | 10/2010 | Lee et al. |
| 7,951,332 B2 | 5/2011 | Cho et al. |
| 7,951,333 B2 | 5/2011 | Lee et al. |
| 7,981,385 B2 | 7/2011 | Park et al. |
| 7,988,915 B2 | 8/2011 | Lee et al. |
| 2005/0221281 A1* | 10/2005 | Ho .................................. 435/4 |
| 2008/0058192 A1 | 3/2008 | Cho et al. |
| 2008/0073546 A1 | 3/2008 | Andersson et al. |
| 2008/0112855 A1 | 5/2008 | Lee et al. |
| 2008/0226504 A1 | 9/2008 | Park et al. |
| 2008/0269077 A1 | 10/2008 | Lee et al. |
| 2009/0209752 A1 | 8/2009 | Peters et al. |
| 2010/0055766 A1 | 3/2010 | Hwang et al. |
| 2010/0068735 A1 | 3/2010 | Kim et al. |
| 2010/0081213 A1 | 4/2010 | Lee et al. |
| 2011/0085950 A1 | 4/2011 | Lee et al. |
| 2011/0121196 A1 | 5/2011 | Yeo et al. |
| 2011/0124128 A1* | 5/2011 | Oosterbroek et al. ........ 436/518 |
| 2011/0131830 A1 | 6/2011 | Inganas et al. |
| 2011/0201101 A1 | 8/2011 | Lee et al. |

FOREIGN PATENT DOCUMENTS

| | | |
|---|---|---|
| TW | 594007 | 6/2004 |
| TW | 201107038 | 3/2011 |
| WO | WO02/43866 | 6/2002 |

OTHER PUBLICATIONS

Mark et, al., "Aliquoting on the centrifugal microfluidic platform based on centrifugo-pneumatic valves", Jan. 8, 2011, pp. 1279-1288, Springer-Verlag.

Ducr'ee et, al., "The centrifugal microfluidic Bio-Disk platform", Jun. 28, 2007, pp. s103-s115, Journal of Micromechanics and Microengineering.

Honda et, al., "Simultaneous Multiple Immunoassays in a Compact Disc—Shaped Microfluidic Device Based on Centrifugal Force", 2005, pp. 1955-1961, Oak Ridge Conference.

Schembri et, al., "Centrifugation and capillarity integrated into a multiple analyte whole blood analyser", May-Jun. 1995, pp. 99-104, vol. 17, Journal of Automatic Chemistry.

Gorkin et, al., "Centrifugal microfluidics for biomedical applications", May 28, 2010, pp. 1758-1773, The Royal Society of Chemistry.

Siegrist, Jonathan et, al., "Serial siphon valving for centrifugal microfluidic platforms", 2010, UC Irvine Postprints, UC Irvine.

Li et, al., "Digitized Molecular Diagnostics: Reading Disk-Based Bioassays with Standard Computer Drives", Nov. 1, 2008, pp. 8216-8223, vol. 80, Analytical Chemistry.

Lai et, al., "Design of a Compact Disk-like Microfluidic Platform for Enzyme-Linked Immunosorbent Assay", Apr. 1, 2004, vol. 76, pp. 1832-1837, Analytical Chemistry.

Brenner et, al., "Frequency-dependent transversal flow control in centrifugal microfluidics", Oct. 14, 2004, pp. 146-150, Lab Chip.

Sergi Morais et, al., "Multiplexed Microimmunoassays on a Digital Versatile Disk", Jul. 15, 2009, vol. 81, pp. 5646-5654, Analytical Chemistry.

Pallapa et, al., "Software-based quantitation of bioassays on CD", May 27, 2010, pp. 620-623, Elsevier B.V..

* cited by examiner

APPARATUS FOR IMMUNOASSAY

CROSS-REFERENCE TO RELATED APPLICATION

This Application claims priority of Taiwan Patent Application No. 101114541, filed on Apr. 24, 2012 and No. 101119292, filed on May 30, 2012 the entirety of which is incorporated by reference herein.

TECHNICAL FIELD

The technical field relates to an immunoassay test apparatus, and more particularly to an immunoassay test apparatus configured with a pin-film assembly and capable of fully mixing magnetic particles with working fluids.

BACKGROUND

Immunoassay is a technology for qualitatively and quantitatively analyzing a substance such as a compound, an enzyme or a protein by using an antibody as a micro biochemical detector, is applicable to quick drug testing, and mainly includes fluorescence immunoassay, radioimmunoassay and enzyme-linked immunosorbent assay (ELISA).

As for types of conventional enzyme immunoassay chips, some prior arts have disclosed a gravity type fluid driving mode, which directly uses an inert fluid to drive the working fluid without providing any power supply, so as to carry out immunoassay on the chips. Some prior arts have disclosed a mode of using a magnetic force to drive magnetic particles, where a movable magnetic unit is used to draw the magnetic particles into intervals of different working fluids for reaction, so as to carry out multi-step immune response.

The above-mentioned conventional patents, although related to immunoassay test technologies, merely have disclosed some technologies respectively. In the method and apparatus adopting the centrifugal force driving mode, reaction of the magnetic particles cannot be utilized. For the mode of using a magnetic force to drive magnetic particles, the magnetic force is used to drive the magnetic particles to enter different reaction tanks for reaction in sequence. Such a structure cannot be implemented in a centrifugal cartridge. Since the magnetic particles are attached and moved on the surface of the reaction tank, the magnetic particles cannot be fully mixed with the fluid in the reaction tank, which affects the precision of assay. Although the magnetic particles are subjected to a washing procedure during movement, the washing effect is undesirable since the magnetic particles are soaked in the fluid. As a result, the magnetic particles may carry residual fluid into a next reaction tank, thereby affecting the result of assay.

SUMMARY

The present disclosure provides an immunoassay test apparatus, comprising a cartridge, a pin-film assembly, a plurality of magnetic particles, at least one first magnetic unit and at least one second magnetic unit.

The cartridge is capable of rotating about a reference axis, and has at least one test unit. The test units comprises a plurality of fluid chambers, a plurality of pin chambers, a microchannel structure, a buffer chamber, a detection chamber, a waste chamber, a capillary U-shaped guiding groove and a gas exhaust structure. Each of the fluid chambers stores a working fluid. Each of the pin chambers is corresponding to one of the fluid chambers, each of the pin chambers is configured with a first sealing film, and the first sealing film is used for preventing the pin chamber from communicating with the fluid chamber. The microchannel structure communicates each of the pin chambers, and the microchannel structure is used for guiding the working fluid to flow from the fluid chamber to the detection chamber. The buffer chamber is connected to the microchannel structure. The detection chamber is in communication with the buffer chamber. The waste chamber is in communication with the detection chamber. The capillary U-shaped guiding groove connects the detection chamber and the waste chamber. The gas exhaust structure is connected to the buffer chamber and the plurality of fluid chambers.

The pin-film assembly comprises a second sealing film, a plurality of pierce mechanisms, and a first actuation unit. The second sealing film is disposed on and covers one surface of the cartridge where the detection chamber is disposed. The plurality of pierce mechanisms is disposed on the second sealing film, each of the pierce mechanisms is corresponding to one of the pin chambers, and each of the pierce mechanisms comprises a pin and a flexible structure. The pin has a first position and a second position. The flexible structure is arranged for allowing the pin to move from the first position to the second position. The first actuation unit is used for driving the pin to move from the first position to the second position, and upon moving from the first position to the second position, the pin pierces the first sealing film, so that the pin chamber is in communication with the fluid chamber.

The plurality of magnetic particles is disposed inside the detection chamber, each of the magnetic particles is capable of magnetic attraction, and each of the magnetic particles has a first marked substance on a surface thereof.

The at least one first magnetic unit is disposed on one side of the detection chamber, the first magnetic unit is used for producing a magnetic field on the plurality of magnetic particles, so as to draw and attach the plurality of magnetic particles to the side of the detection chamber where the first magnetic unit is disposed.

The at least one second magnetic unit is capable of moving reciprocatingly between a third position and a fourth position. A magnetic force of the second magnetic unit is larger than that of the first magnetic unit. When the second magnetic unit is located at the fourth position, the second magnetic unit is located on one side of the detection chamber opposite to the first magnetic unit, and the second magnetic unit produces a magnetic field on the plurality of magnetic particles, so as to draw and attach the plurality of magnetic particles to the side of the detection chamber where the second magnetic unit is disposed.

In order to enable the Examiner to have a further understanding and recognition of the objectives and efficacies of the present disclosure, the present disclosure is described in detail below with reference to the accompanying drawings.

DETAILED DESCRIPTION OF DISCLOSED EMBODIMENTS

Figure 1:
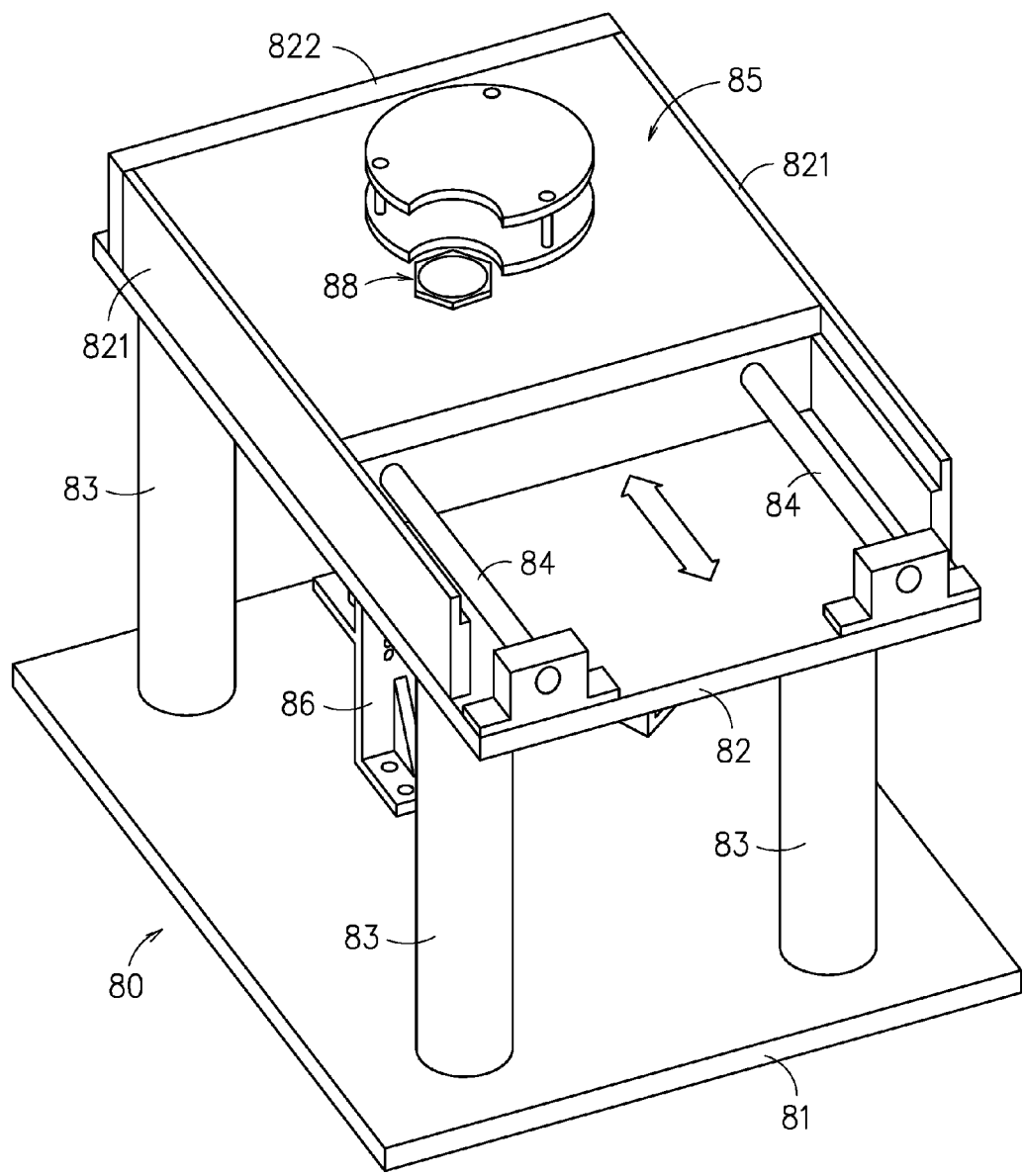
FIG. 1 is a three-dimensional assembled structural outside view according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing. Referring to FIG. 1 to FIG. 4, an immunoassay test apparatus provided by the present disclosure mainly includes a cartridge 10, a tray 20 and a pin-film assembly 50. The tray 20 is used for holding the cartridge 10. The pin-film assembly 50 is disposed on a surface of the cartridge 10 opposite to the tray 20. The cartridge 10, the tray 20 and the pin-film assembly 50 are disposed on a support frame structure 80.

Figure 5:
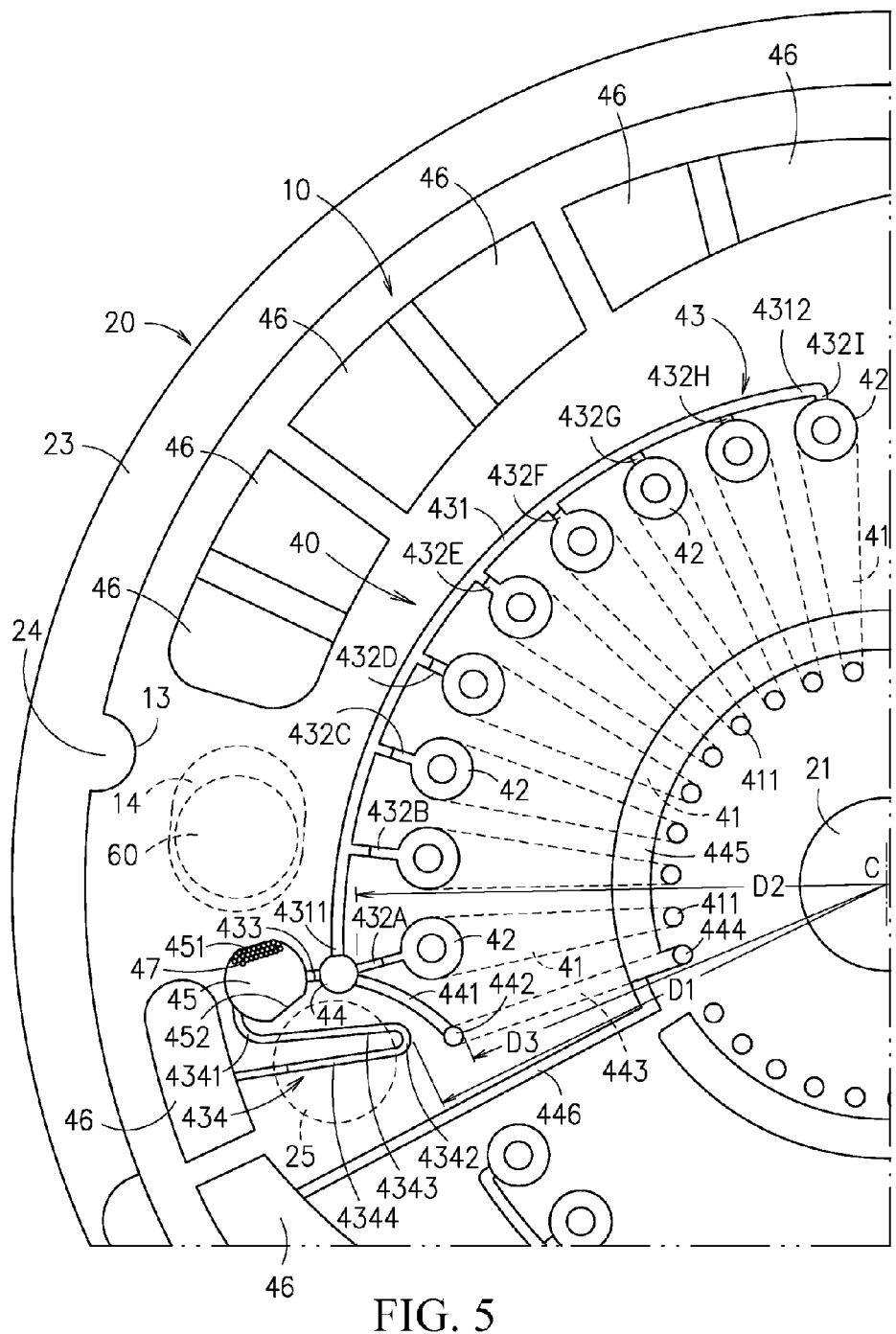
FIG. 5 is a partial schematic structural top view of a cartridge according to an embodiment of the present disclosure.
Figure 6:
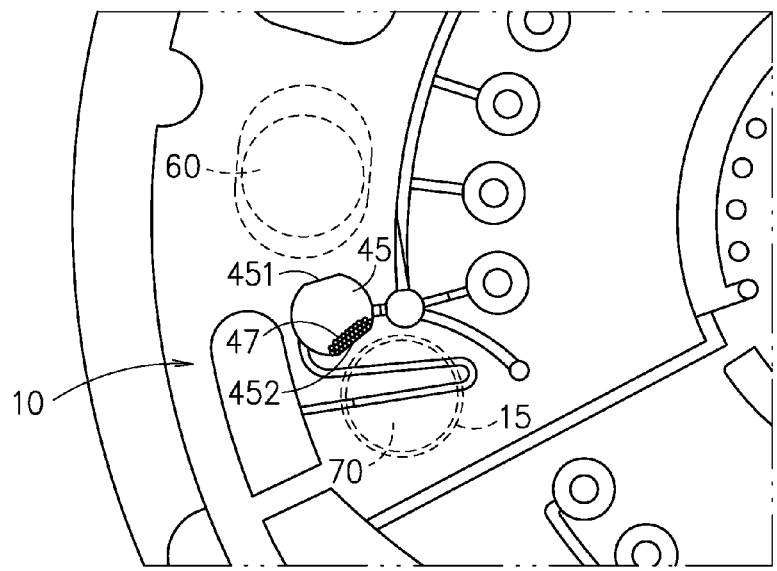
FIG. 6 is a schematic structural top view illustrating movement of magnetic particles to a second side wall of a detection chamber according to an embodiment of the present disclosure.
Figure 7:
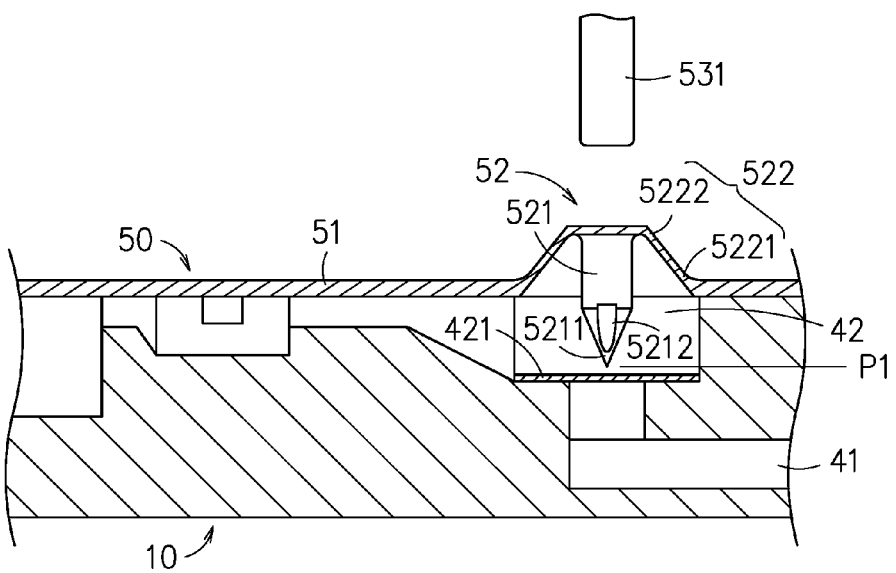
FIG. 7 is a schematic assembled sectional structural view of a pin-film assembly and a cartridge according to the present disclosure.

Referring to FIG. 4 to FIG. 7, the cartridge 10 of the present disclosure exhibits a flat disk shape. Three test units 40 are disposed on the cartridge 10, where the three test units 40 are arranged in an annular array centered on a reference axis C. Each of the test units 40 includes nine fluid chambers 41, nine pin chambers 42, a microchannel structure 43, a buffer chamber 44, a detection chamber 45 and a waste chamber 46. The three test units 40 are capable of performing an immunoassay on three specimens respectively, with each specimen undergoing nine processes including sampling, reaction and washing. The fluid chambers 41 are disposed inside the cartridge 10, each of the fluid chambers 41 has a first gas exhaust hole 411, and the plurality of first gas exhaust holes 411 is disposed centered on and around the reference axis C. The pin chambers 42, the microchannel structure 43, the detection chamber 45 and the waste chamber 46 are all disposed on a top surface of the cartridge 10. Each of the fluid chambers 41 is used for storing a working fluid, which is set according to different test items to be analyzed, where the working fluid may be an antibody-bound magnetic particle, diluted blood, a washing buffer, an enzyme-labeled detection antibody or an enzyme-substrate hydrolysis developing solution, or a washing solution. The plurality of pin chambers 42 is disposed centered on and around the reference axis C. Each of the pin chambers 42 is corresponding to one of the fluid chambers 41 and one of the first gas exhaust holes 411. Each of the pin chambers 42 is configured with a first sealing film 421 (as shown in FIG. 7), and if the first sealing film 421 is not damaged, the first sealing film 421 is capable of preventing the pin chamber 42 from communicating with the fluid chamber 41, so that the working fluid inside the fluid chamber 41 does not flow into the pin chamber 42.

Figure 4:
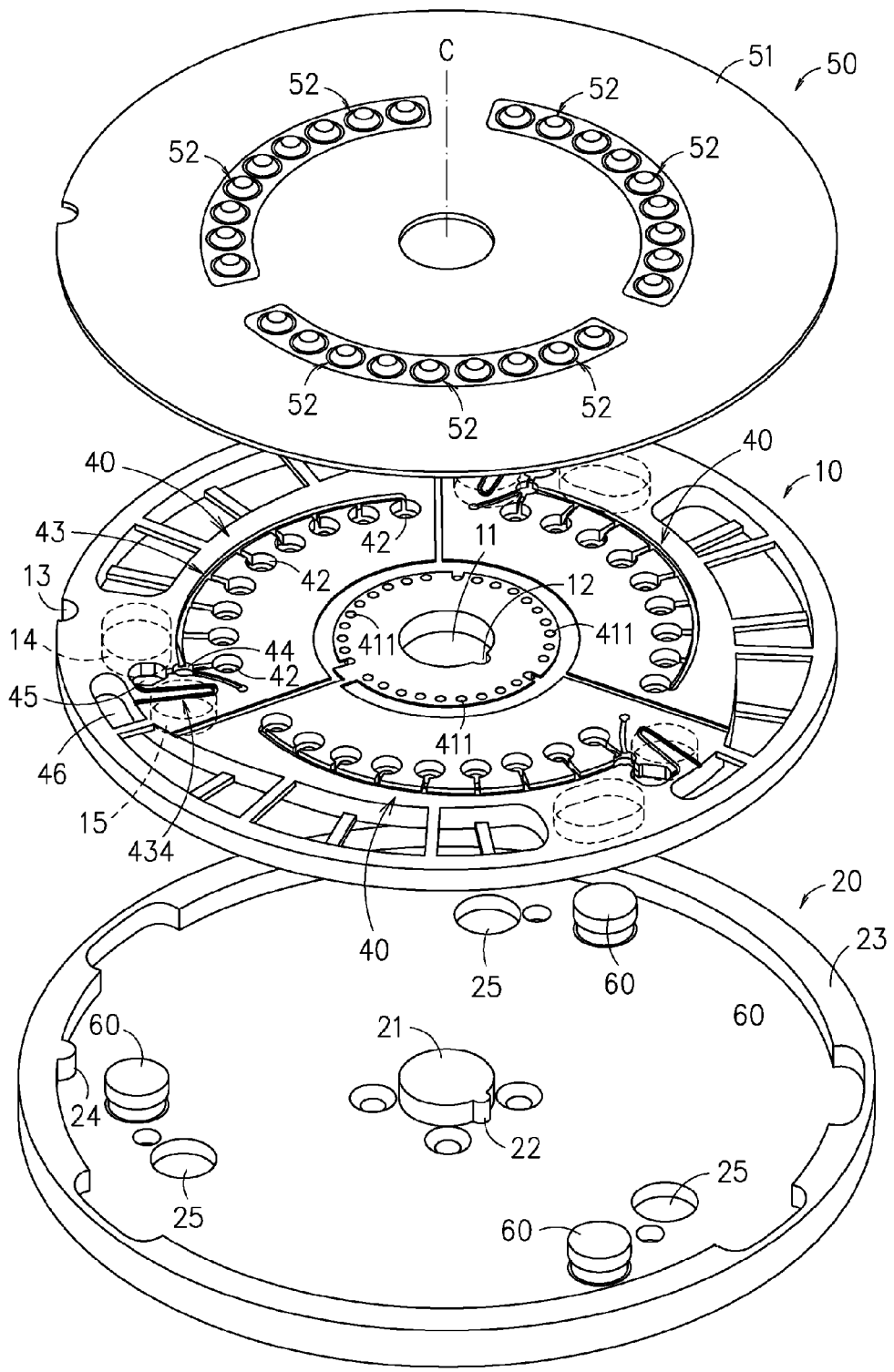
FIG. 4 is a schematic exploded structural view of a tray, a cartridge and a pin-film assembly according to an embodiment of the present disclosure.

Referring to FIG. 4 and FIG. 5, the microchannel structure 43 is used for communicating each of the pin chambers 42. The microchannel structure 43 includes a first microchannel 431, a plurality of second microchannels 432A-432I and a third microchannel 433. The first microchannel 431 has a radian, a center of a circle of the radian of the first microchannel 431 is disposed eccentric to the reference axis C, and the three first microchannels 431 are disposed centered on the reference axis C to gradually expand outwards in a radiated form. Each of the second microchannels 432A-432I extends radially about the reference axis C, each of the second microchannels 432A-432I has two opposite ends, one end of each of the second microchannels 432A-432I is connected to the first microchannel 431, and an other end of each of the second microchannels 432A-432I is connected to one of the pin chambers 42. The first microchannel 431 has a first end 4311 and a second end 4312 opposite to each other, the second microchannel 432A is disposed at the first end 4311 of the first microchannel 431, the second microchannel 432I is disposed at the second end 4312 of the first microchannel 431, and the plurality of second microchannels 432A-432I has a length gradually decreasing from the first end 4311 of the first microchannel 431 to the second end 4312 of the first microchannel 431, that is, the second microchannel 432A is the longest and the second microchannel 432I is the shortest. The buffer chamber 44 is disposed at the first end 4311 of the first microchannel 431. The third microchannel 433 extends radially about the reference axis C, one end of the third microchannel 433 is connected to the buffer chamber 44, and an other end of the third microchannel 433 is connected to the detection chamber 45, so that the detection chamber 45 is in communication with the buffer chamber 44. The buffer chamber 44 is connected to one end of a first gas exhaust passage 441, an other end of the first gas exhaust passage 441 is connected to a second gas exhaust hole 442, and a distance D3 from the second gas exhaust hole 442 to the reference axis C is smaller than a distance D2 from the buffer chamber 44 to the reference axis C. The second gas exhaust hole 442 is connected to a third gas exhaust hole 444 through a second gas exhaust passage 443, and the second gas exhaust passage 443 is disposed inside the cartridge 10. In this embodiment, a distance from the third gas exhaust hole 444 to the reference axis C is equal to that from the plurality of first gas exhaust holes 411 to the reference axis C. The third gas exhaust hole 444 is connected to an annular gas exhaust chamber 445. In this embodiment, the annular gas exhaust chamber 445 is annularly disposed at peripheries of the first gas exhaust hole 411 and the third gas exhaust hole 444 around the reference axis C. The annular gas exhaust chamber 445 is connected to one end of a third gas exhaust passage 446, and an other end of the third gas exhaust passage 446 extends away from the reference axis C and is connected to the waste chamber 46. The first gas exhaust hole 411, the first gas exhaust passage 441, the second gas exhaust hole 442, the second gas exhaust passage 443, the third gas exhaust hole 444, the annular gas exhaust chamber 445, and the third gas exhaust passage 446 form a gas exhaust structure of the present disclosure.

In addition, the waste chamber 46 is connected to the detection chamber 45 through a capillary U-shaped guiding groove 434, and is connected to the third microchannel 433. The capillary U-shaped guiding groove 434 includes a first arc-shaped groove 4341, a second arc-shaped groove 4342, a first connection groove 4343 and a second connection groove 4344. The first arc-shaped groove 4341, the second arc-shaped groove 4342, the first connection groove 4343 and the second connection groove 4344 respectively have two opposite ends. One end of the first arc-shaped groove 4341 is connected to the detection chamber 45, and an other end of the first arc-shaped groove 4341 is bent towards a center of the cartridge 10 and is connected to one end of the first connection groove 4343. The first connection groove 4343 extends for a length towards the center of the cartridge 10, and an other end of the first connection groove 4343 is connected to one end of the second arc-shaped groove 4342. The two opposite ends of the second arc-shaped groove 4342 depart from the center of the cartridge 10, the second arc-shaped groove 4342 has a convex arc surface, the convex arc surface faces the reference axis C, and a distance D1 from the convex arc surface to the reference axis C is smaller than the distance D2 from the buffer chamber 44 to the reference axis C. An other end of the second arc-shaped groove 4342 is connected to one end of the second connection groove 4344. The second connection groove 4344 extends for a length away from the center of the cartridge 10, and an other end of the second connection groove 4344 is connected to the waste chamber 46. The first arc-shaped groove 4341, the first connection groove 4343, the second arc-shaped groove 4342, and the second connection groove 4344 are connected in series to form a capillary U-shaped guiding groove 434 of a U-shaped structure.

A plurality of magnetic particles 47 is disposed inside the detection chamber 45. Each of the magnetic particles 47 is capable of magnetic attraction, and each of the magnetic particles 47 has a first marked substance on a surface thereof. The first marked substance may be a conjunctive nucleic acid (DNA or RNA), a protein, a biomarker, an antibody, a cell, or a biomolecule.

Figure 2:
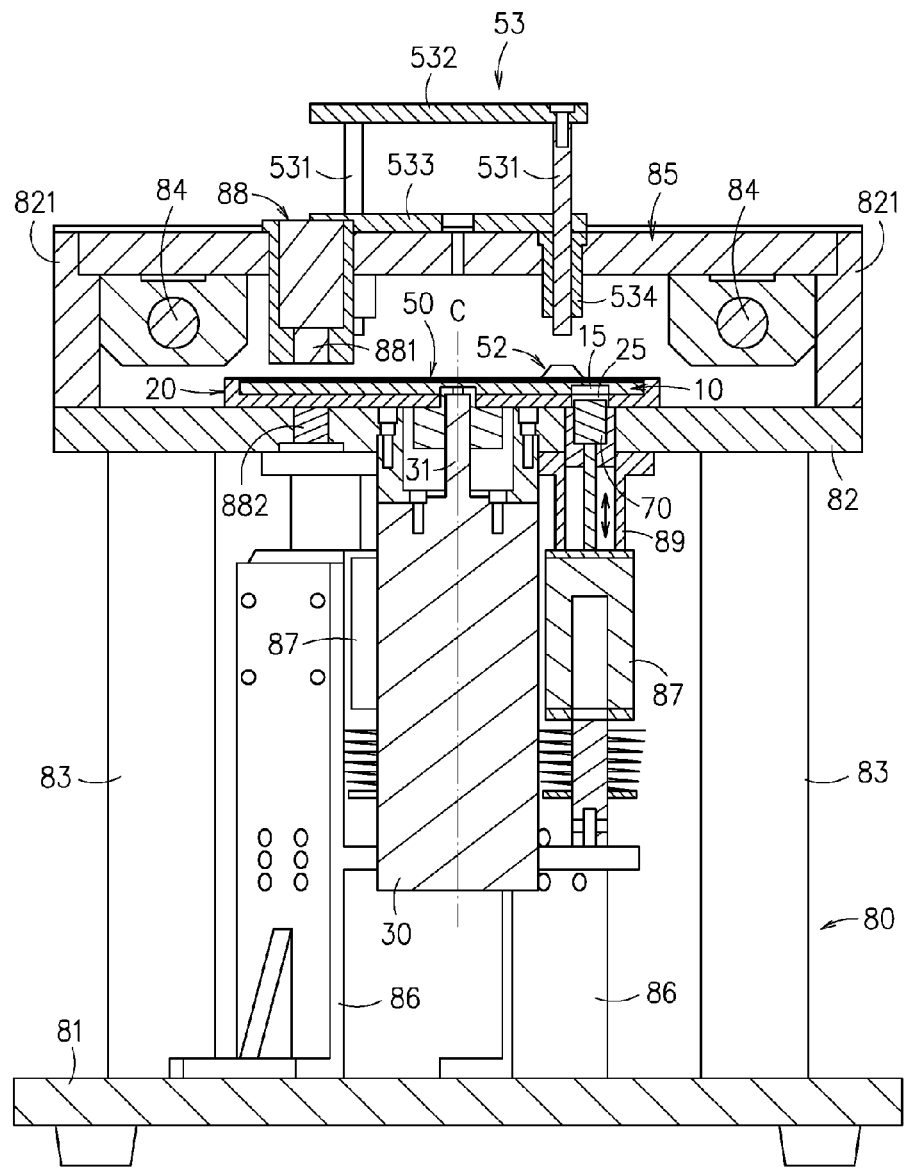
FIG. 2 is a schematic sectional structural view according to an embodiment of the present disclosure.
Figure 3:
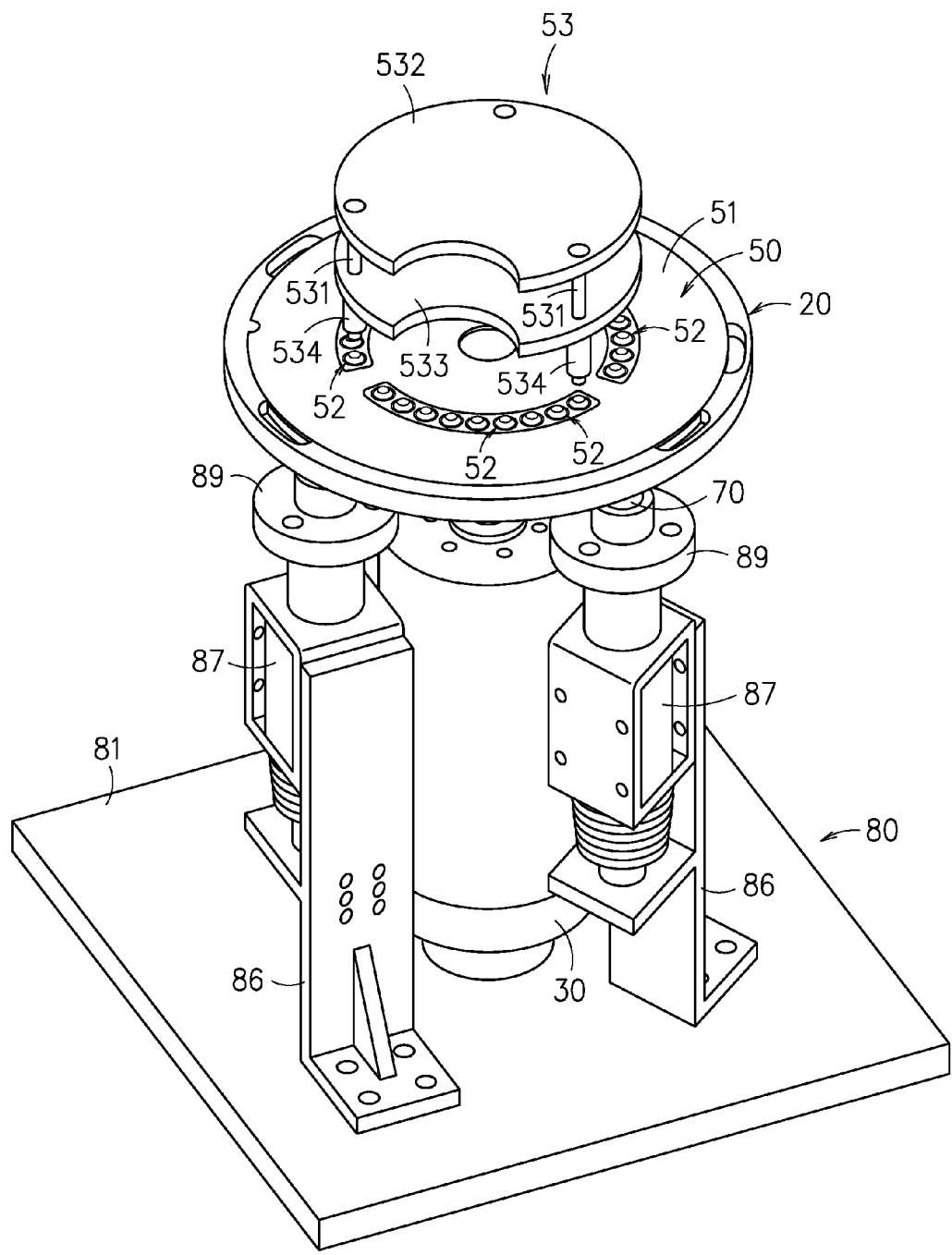
FIG. 3 is a partial assembled three-dimensional structural view according to an embodiment of the present disclosure.

Referring to FIG. 4 and FIG. 5, a connection structure is disposed between the tray 20 and the cartridge 10 of the present disclosure. In this embodiment, a protruding cylinder 21 is disposed at a center of the tray 20, a semicircular protruding portion 22 is disposed on an outer side of the protruding cylinder 21, a collar 23 is disposed around the tray 20, a semicircular protruding portion 24 is disposed on an inner side wall of the collar 23, and a hollow portion 11 and semicircular recessed portions 12, 13 are disposed on the cartridge 10 at positions corresponding to the protruding cylinder 21 and the semicircular protruding portions 22, 24. The cartridge 10 is embedded on the tray 20. Through the engagement between the hollow portion 11 and the protruding cylinder 21 and between the semicircular recessed portions 12, 13 and the semicircular protruding portions 22, 24, the cartridge 10 can be positioned on the tray 20. Referring to FIG. 2 and FIG. 3, the cartridge 10 and the tray 20 are connected to a driving motor 30. The driving motor 30 has a driving shaft 31, and the cartridge 10 and the tray 20 use the driving shaft 31 as the reference axis C. When the driving motor 30 operates, the cartridge 10 and the tray 20 are capable of rotating synchronously about the driving shaft 31. It should be noted that, the semicircular recessed portions 12, 13 and the semicircular protruding portions 22, 24 are merely described as one embodiment of a connection structure between the tray 20 and the cartridge 10, and other connection structures such as a slot-hook structure and a screw-hole structure also can achieve synchronous rotation of the tray 20 and the cartridge 10. Secondly, a first magnetic unit 60 is disposed on one side of the detection chamber 45. The first magnetic unit 60 protrudes from a surface of the tray 20 where the cartridge 10 is disposed, a first recess 14 is formed in the cartridge 10 at a position corresponding to the first magnetic unit 60, and the first magnetic unit 60 is embedded in the first recess 14.

Referring to FIG. 3, FIG. 4 and FIG. 7, the pin-film assembly 50 of the present disclosure includes a second sealing film 51, a plurality of pierce mechanisms 52 and a first actuation unit 53. The second sealing film 51 is disposed on and covers one surface of the cartridge 10 where the detection chamber 45 is disposed (that is, the top surface of the cartridge 10). The second sealing film 51 and the first sealing film 421 may be formed of a composite material of an aluminum film and an acrylic film, a tin foil, a copper foil, an acrylic film, polycarbonate (PC), a polyethylene (PE) film, a polyurethane (PU) film, a polypropylene (PP) film, a polyetheretherketone (PEEK) film or a polyethylene terephthalate (PET) film. The plurality of pierce mechanisms 52 is disposed on the second sealing film 51, each of the pierce mechanisms 52 is corresponding to one of the pin chambers 42, and each of the pierce mechanisms 52 includes a pin 521 and a flexible structure 522. One end of the pin 521 facing the cartridge 10 is a tapered structure 5211, at least one guide slot 5212 is formed in a surface of the tapered structure 5211, and the guide slot 5212 extends for a length parallel to an axial direction of the pin 521. The flexible structure 522 is a conical cylindrical structure, and the flexible structure 522 is formed of a flexible material, or a flexible and elastic material. The flexible structure 522 has a first end 5221 and a second end 5222 opposite to each other in an axial direction thereof, the first end 5221 of the flexible structure 522 has an outer diameter larger than that of the second end 5222 of the flexible structure 522, a pore is formed in the second sealing film 51 at a position corresponding to each of the pin chambers 42, the first end 5221 of the flexible structure 522 is connected to the pore, the second end 5222 of the flexible structure 522 protrudes from a surface of the second sealing film 51 opposite to the cartridge 10, the pin 521 has two opposite ends, one end of the pin 521 is connected to the second end 5222 of the flexible structure 522, and the end of the pin 521 where the tapered structure 5211 is disposed faces the cartridge 10.

Figure 11:
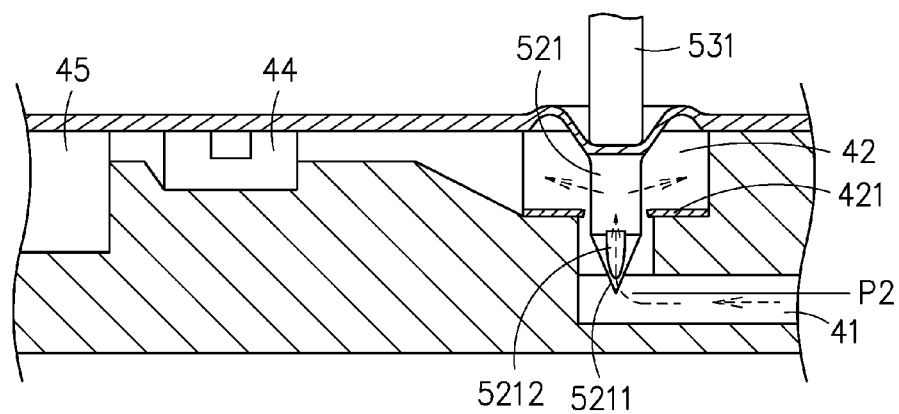

Referring to FIG. 2 and FIG. 3, the first actuation unit 53 has a function of driving the pin 521 to move. In this embodiment, the first actuation unit 53 mainly includes at least one push rod 531, a first plate 532, and a second plate 533. Since the cartridge 10 includes the three test units 40 (as shown in FIG. 4), the first actuation unit 53 is configured with three push rods 531, where the three push rods 531 are disposed on a bottom of the first plate 532, and the second plate 533 is disposed between the first plate 532 and the pierce mechanism 52. A sleeve 534 is disposed on the second plate 533 at a position corresponding to each of the push rods 531, the push rod 531 extends through the sleeve 534, an axial end of the push rod 531 faces the pierce mechanism 52, and the second plate 533 is fixed to a top of the support frame structure 80. The push rod 531 is used in combination with a first actuator (not shown). The first actuator presses the first plate 532 downwards to simultaneously drive the three push rods 531 to move axially, so that the push rods 531 move relative to the pierce mechanism 52. The push rod 531 pushes the pin 521 to move axially from a first position P1 (a position of the pin 521 as shown in FIG. 7) to a second position P2 (a position of the pin 521 as shown in FIG. 11). When the first actuator is lifted, and the action force of the push rod 531 to the pin 521 is released, if the flexible structure 522 fails to return to the first position P1 (the position of the pin 521 as shown in FIG. 7) due to plastic deformation, the cartridge 10 is rotated, so that under a centrifugal force, the working fluid sealed in the pin chamber 42 is discharged from the guide slot 5212 of the tapered structure 5211 to the detection chamber 45 through the microchannel 431. In another possible case, when the first actuation unit 53 is lifted, and the action force of the push rod 531 to the pin 521 is released, the flexible structure 522 may provide an elastic force for the pin 521, so as to enable the pin 521 to automatically return from the second position P2 (the position of the pin 521 as shown in FIG. 11) to the first position P1 (the position of the pin 521 as shown in FIG. 7). At this time, the cartridge 10 is rotated, and under a centrifugal force, the working fluid sealed in the pin chamber 42 is discharged from the pore of the first sealing film 421 to the detection chamber 45 through the microchannel 431. The above two cases, where the flexible structure 522 fails to return to the first position P1 due to plastic deformation and the flexible structure 522 may provide an elastic force to enable the pin 521 to automatically return from the second position P2 to the first position P1, are dependent on the material of the flexible structure 522 and practical operation conditions. For example, when the first actuation unit 53 is lifted, and the action force of the push rod 531 to the pin 521 is released, if the flexible structure 522 is formed of a flexible material, the pin 521 does not automatically return to the first position P1, and the working fluid in the pin chamber 42 is discharged from the guide slot 5212 of the tapered structure 5211 to the detection chamber 45 through the microchannel 431; and when the flexible structure 522 is formed of a flexible and elastic material, since the flexible structure 522 is capable of carrying the pin 521 to automatically return to the first position P1, the working fluid in the pin chamber 42 is discharged from the pore of the first sealing film 421 to the detection chamber 45 through the microchannel 431. In other words, the flexible structure 522 may be replaced with an elastic structure, where the elastic structure provides a plastic deforming force and has an elastic restoring force. The type and form of the first actuator are not particularly limited, for example, a manual clamp may be disposed at a central top portion of the first plate 532, so as to use the manual clamp to press the first plate 532.

Figure 8:
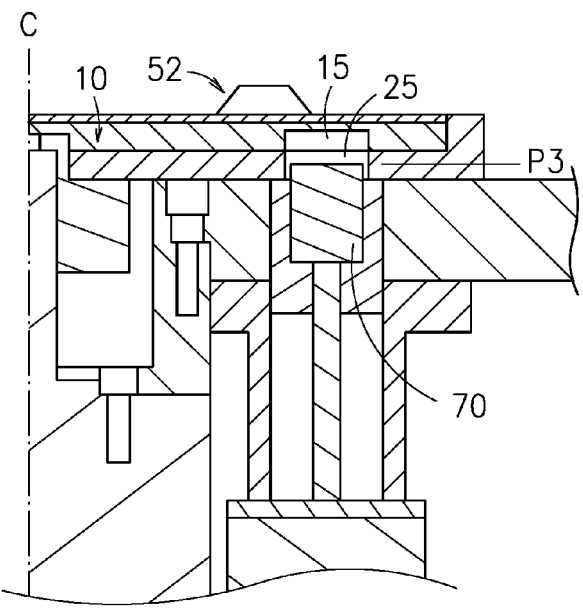
FIG. 8 is a schematic assembled sectional structural view of a second magnetic unit being located at a third position according to the present disclosure.
Figure 9:
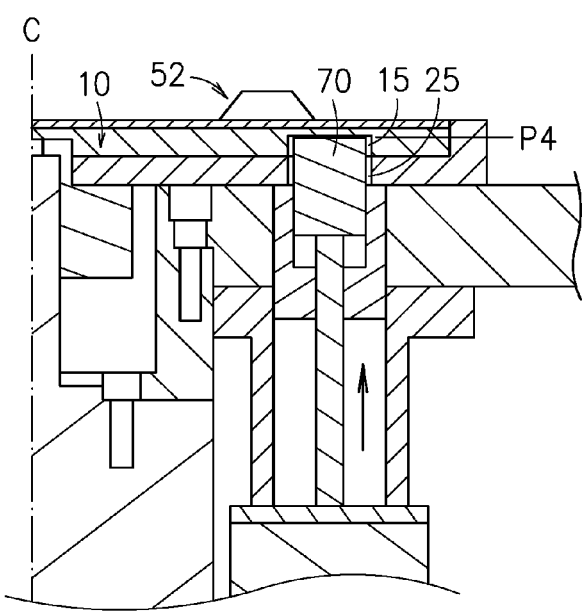
FIG. 9 is a schematic assembled sectional structural view of a second magnetic unit being located at a fourth position according to the present disclosure.

Referring to FIG. 1, FIG. 2, FIG. 8 and FIG. 9, the support frame structure 80 of the present disclosure includes a base 81, a test platform 82, a plurality of support columns 83, a plurality of guide rods 84, a darkroom structure 85 and a plurality of fixed brackets 86. The test platform 82 is used for holding the tray 20. The plurality of support columns 83 is disposed between the base 81 and the test platform 82. The plurality of support columns 83 is used for supporting the test platform 82. The plurality of guide rods 84 and the darkroom structure 85 are disposed on a surface of the test platform 82 where the tray 20 is disposed. The darkroom structure 85 is used for covering the tray 20 and the cartridge 10 disposed on the tray 20. The darkroom structure 85 is connected to the plurality of guide rods 84. In this embodiment, the plurality of guide rods 84 extends through the darkroom structure 85. Alternatively, the guide rods 84 may be disposed outside the darkroom structure 85. The darkroom structure 85 is capable of moving reciprocatingly in an axial direction of the guide rod 84, and the darkroom structure 85 may be electrically controlled to slide, or may be configured with a handle for a user to manually slide the darkroom structure 85, so that the cartridge 10 is enclosed in the darkroom structure 85 or exposed out of the darkroom structure 85, thereby facilitating the user to install or replace the cartridge 10. At least one optical detection system 88 is disposed at the darkroom structure 85, where the optical detection system 88 includes an excitation light source (not shown), an optical fiber splice 881 and an optical light-receiving element 882. The excitation light source is used for providing a light ray, the optical fiber splice 881 is used for guiding the light ray into the detection chamber 45 of the cartridge 10 (referring to FIG. 4), and the optical light-receiving element 882 is used for detecting transmittance. Each of the fixed bracket 86 is configured with a second actuator 87. Each of the second actuators 87 is connected to a second magnetic unit 70, and the second actuator 87 drives the second magnetic unit 70 to move vertically in a reciprocating manner between a third position P3 (a position of the second magnetic unit 70 as shown in FIG. 8) and a fourth position P4 (a position of the second magnetic unit 70 as shown in FIG. 9). A through hole 25 is formed in the tray 20, a second recess 15 is formed in the cartridge 10 at a position corresponding to the through hole 25, and a second magnetic unit 70 is disposed correspondingly at the position of the through hole 25 and the second recess 15. A magnetic force of the second magnetic unit 70 is larger than that of the first magnetic unit 60, and the second magnetic unit 70 is disposed on a surface of the tray 20 opposite to the cartridge 10 (that is, a bottom surface of the cartridge 10). When the second magnetic unit 70 is located at the third position P3, the second magnetic unit 70 is located below the cartridge 10 (the position of the second magnetic unit 70 as shown in FIG. 8), and when the second magnetic unit 70 is lifted to the fourth position P4 (the position of the second magnetic unit 70 as shown in FIG. 9), the second magnetic unit 70 extends through the through hole 25 and is located inside the second recess 15.

Referring to FIG. 1 to FIG. 3, a light shield 89 is disposed between the second actuator 87 and the test platform 82, where the light shield 89 is used for blocking a gap between the second actuator 87 and the test platform 82, so as to prevent the light ray inside the darkroom structure 85 from leaking out of the darkroom structure 85. In addition, in this embodiment, each of two sides of the test platform 82 corresponding to a sliding direction of the darkroom structure 85 is configured with a first baffle 821, and two sides of the darkroom structure 85 corresponding to facing side surfaces of the two first baffles 821 are design into a step-like structure with a wide upper side and a narrow lower side, so as to prevent light leakage from the two sides of the darkroom structure 85. In addition, a second baffle 822 is disposed on one end portion of the test platform 82 in the sliding direction of the darkroom structure 85, and mutually attracting magnetic units (not shown) may be disposed between the second baffle 822 and the darkroom structure 85, so that the second baffle 822 and the darkroom structure 85 are fixed through magnetic attraction, as shown in FIG. 1. Whereby, the cartridge 10 can complete all immunoassay and optical detection operations inside the darkroom structure 85. It should be noted that, the shape and specific structure of the darkroom structure 85 of the present disclosure are not particularly limited, as long as the cartridge 10 is enclosed in the darkroom structure 85 and light leakage is avoided.

Referring to FIG. 2, FIG. 5 and FIG. 6, a relative relationship between the first magnetic unit 60, the second magnetic unit 70 and the detection chamber 45 of the present disclosure is illustrated. The first magnetic unit 60 of the present disclosure is fixedly disposed on one side of the detection chamber 45. When the second magnetic unit 70 is located at the third position P3, the second magnetic unit 70 is located below the cartridge 10 (the position of the second magnetic unit 70 as shown in FIG. 8), and the second magnetic unit 70 does not produce a magnetic field on the magnetic particles 47 inside the detection chamber 45, but the first magnetic unit 60 produces a magnetic field on the magnetic particles 47 inside the detection chamber 45, so as to draw, collect and attach the magnetic particles 47 to the side of the detection chamber 45 where the first magnetic unit 60 is disposed, as shown in FIG. 5. When the second magnetic unit 70 is lifted to the fourth position P4, the second magnetic unit 70 extends through the through hole 25 and is located inside the second recess 15, as the position of the second magnetic unit 70 shown in FIG. 9, and the second magnetic unit 70 is located on one side of the detection chamber 45 opposite to the first magnetic unit 60. Since the magnetic force of the second magnetic unit 70 is larger than that of the first magnetic unit 60, the second magnetic unit 70 produces a magnetic field on the magnetic particles 47, so as to draw and attach the magnetic particles 47 to the side of the detection chamber 45 where the second magnetic unit 70 is disposed, as shown in FIG. 6. When the second magnetic unit 70 is lowered to the third position P3 (the position of the second magnetic unit 70 as shown in FIG. 8), the magnetic field produced on the magnetic particles 47 by the second magnetic unit 70 is reduced, and the magnetic force of the second magnetic unit 70 to the magnetic particles 47 is smaller than that of the first magnetic unit 60 to the magnetic particles 47, so that the magnetic particles 47 can be drawn to an other side of the detection chamber 45 by the first magnetic unit 60. Through the reciprocating vertical movement of the second magnetic unit 70, the magnetic particles 47 can be driven to move inside the detection chamber 45 in a reciprocating manner. In order to enable the magnetic particles 47 to be attached to a surface of an inner side wall of the detection chamber 45 more uniformly, a first side wall 451 is disposed on one side of the detection chamber 45 adjacent to the first magnetic unit 60, a second side wall 452 is disposed on one side of the detection chamber 45 adjacent to the second magnetic unit 70, and the first side wall 451 and the second side wall 452 are planes.

The magnetic forces of the first magnetic unit 60 and the second magnetic unit 70 of the present disclosure may be designed according to different practical requirements. Table 1 shows magnetic force data obtained through measurement at different positions in a specific embodiment where permanent $Nd_2Fe_{14}B$ magnets of different sizes are used as the first magnetic unit 60 and the second magnetic unit 70 of the present disclosure.

TABLE 1

Measured data of magnetic force and distance of permanent magnetic unit

| Distance | Magnetic force (Gauss) | |
| --- | --- | --- |
| | Diameter 8 mm × 2 mm (height) | Diameter 8 mm × 10 mm (height) |
| 0 mm | 2770 | 4830 |
| 1 mm | 2020 | 3560 |
| 2 mm | 1398 | 2540 |
| 3 mm | 493 | 2040 |
| 5 mm | 389 | 1230 |
| 8 mm | 149 | 454 |
| 10 mm | 96 | 270 |

Here, 0 mm represents the magnet surface, where the magnetic force is the largest. As the distance increases, the magnetic force gradually decreases. In the present disclosure, a permanent $Nd_2Fe_{14}B$ magnet of diameter 8 mm×2 mm is used as the first magnetic unit 60, and fixed on the tray 20, a distance from the permanent $Nd_2Fe_{14}B$ magnet to the magnetic particles is about 2.5 mm, and the magnetic force is 946 Gauss, which is sufficient to draw and maintain the magnetic particles 47 on the first side wall 451 of the detection chamber 45. In addition, a permanent $Nd_2Fe_{14}B$ magnet of diameter 8 mm×10 mm is used as the second magnetic unit 70, and fixed on the second actuator 87. When the second magnetic unit 40 is lifted to the fourth position P4 (the position of the second magnetic unit 70 as shown in FIG. 9), the shortest distance to the magnetic particles 47 is about 1.5 mm, and the magnetic force is 3050 Gauss. Since the magnetic force of the second magnetic unit 70 is larger than that of the first magnetic unit 60, the magnetic particles 47 are drawn to the side of the detection chamber 45 adjacent to the second magnetic unit 70, that is, the magnetic particles 47 are moved from the first side wall 451 to the second side wall 452 of the detection chamber 45. When the second magnetic unit 70 is lowered and the shortest distance to the magnetic particles 47 exceeds 10 mm, the magnetic force of the second magnetic unit 70 is smaller than 270 Gauss, and accordingly, the magnetic particles 47 are drawn back to the first side wall 451 of the detection chamber 45 by the first magnetic unit 60.

Referring to FIG. 1 to FIG. 4, the working fluid of the present disclosure is sealed in the cartridge 10 in advance, and the top surface of the cartridge 10 is covered with the pin-film assembly 50, so that the cartridge 10 forms a sealed structure, thereby protecting the working fluid from contamination. After the cartridge 10 is delivered to the user and installed on the tray 20, the darkroom structure 85 is slid, so that the cartridge 10 is enclosed in the darkroom structure 85. The three push rods 531 are positioned in the corresponding pin chambers 42 respectively, and then driven to move downwards.

Figure 10:
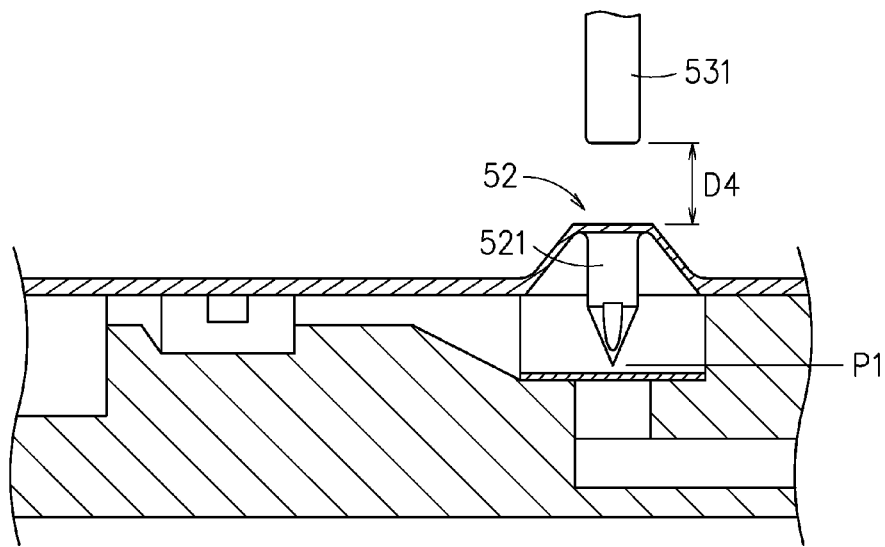
FIG. 10 to FIG. 13 are schematic sectional structural views illustrating continuous operation of a pin-film assembly piercing a first sealing film according to an embodiment of the present disclosure.
Figure 12:
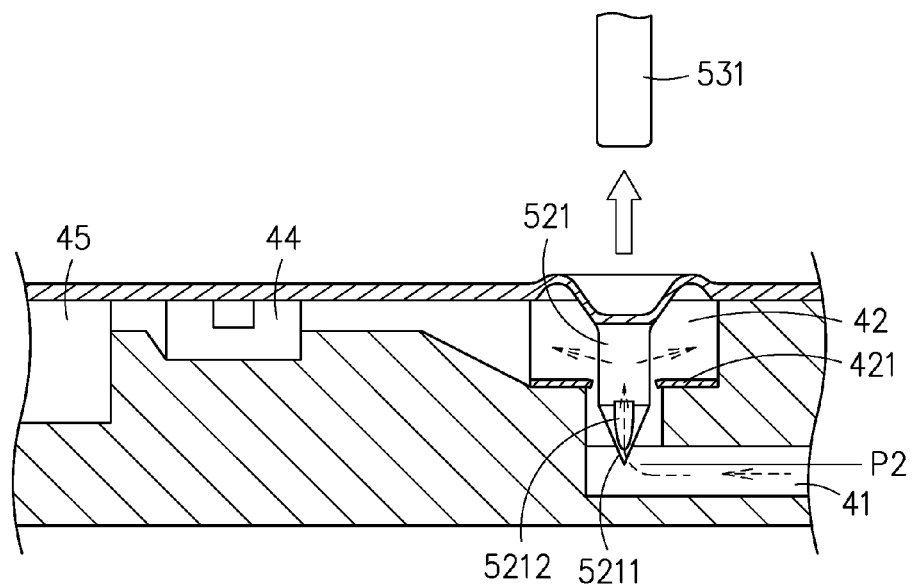
Figure 13:
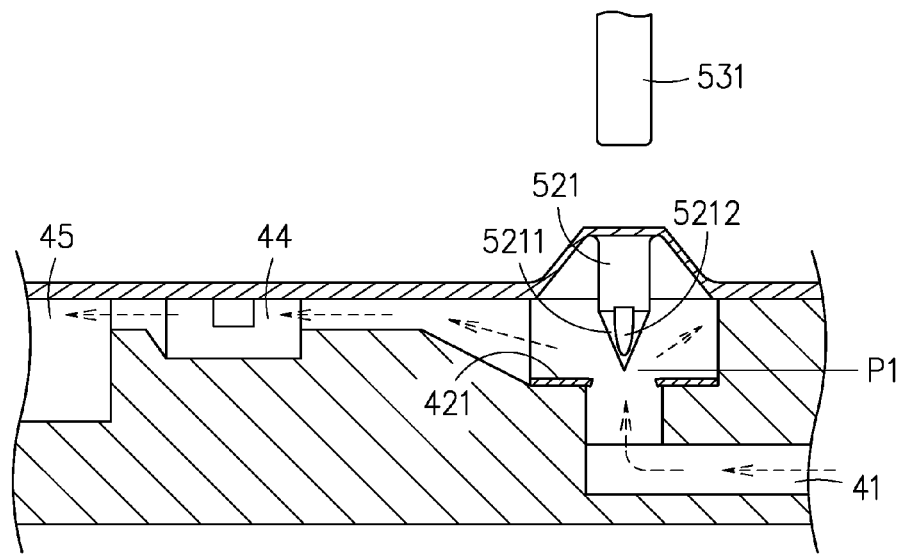

FIG. 10 to FIG. 13 illustrates processes of continuous operation of the pin-film assembly 50 of the present disclosure. Referring to FIG. 10, when the push rod 531 is not actuated, a distance D4 exists between the push rod 531 and the pierce mechanism 52, and the pin 521 is located at the first position P1. Referring to FIG. 11, when the push rod 531 is actuated to push the pin 521 downwards, the pin 521 is moved downwards from the first position P1 shown in FIG. 10 to the second position P2, and once the pin 521 is moved to the second position P2, the tapered structure 5211 of the pin 521 pierces the first sealing film 421, so that the pin chamber 42 is in communication with the fluid chamber 41. At this time, referring to FIG. 5 and FIG. 11, the first gas exhaust hole 411, the plurality of fluid chambers 41, the plurality of pin chambers 42, the microchannel structure 43, the buffer chamber 44, the first gas exhaust passage 441, the second gas exhaust hole 442, the second gas exhaust passage 443, the third gas exhaust hole 444, the annular gas exhaust chamber 445, the third gas exhaust passage 446 and the waste chamber 46 form a closed path. Through the centrifugal force generated during rotation of the cartridge 10, when the first sealing film 421 is pierced, the working fluid (indicated by dashed arrows shown in FIG. 11) may be guided by the guide slot 5212 to flow into the pin chamber 42. Referring to FIG. 12, when the push rod 531 is lifted to be detached from the pin 521, the pin 521 is still maintained at the second position P2 for a while, and at this time, the working fluid may still be guided by the guide slot 5212 to continuously flow into the pin chamber 42. Referring to FIG. 13, after a period of time after the push rod 531 is detached from the pin 521, the elastic function of the flexible structure 522 allows the pin 521 to automatically move upwards to the first position P1. The second sealing film 51 will not be broken when the pin 521 is pressed and detached, thereby preventing the working fluid from splashing in the centrifugal process. Through the centrifugal force generated during rotation of the cartridge 10, the working fluid continuously flows from the pin chamber 42 towards the buffer chamber 44 to enter the detection chamber 45. A gas generated when the working fluid flows from the pin chamber 42 to the detection chamber 45 may be discharged through the first gas exhaust passage 441 (as shown in FIG. 5).

Referring to FIG. 1 to FIG. 4, when the working fluid reaches the detection chamber 45, the cartridge 10 is stopped, the second magnetic unit 70 is driven to move vertically in a reciprocating manner. Through the magnetic force interaction between the first magnetic unit 60 and the second magnetic unit 70, the magnetic particles 47 are moved to-and-fro in the detection chamber 45 (as shown in FIG. 5 and FIG. 6), so that the magnetic particles 47 are uniformly mixed with the working fluid. The first marked substance on the surface of the magnetic particle 47 may react with the working fluid. After mixing is finished, the second magnetic unit 70 is driven to stop moving reciprocatingly, and the second magnetic unit 70 is lowered to the third position P3 distal from the magnetic particles 47 (the position of the second magnetic unit 70 as shown in FIG. 8), and the magnetic particles 47 are drawn on the first side wall 451 of the detection chamber 45 by the first set as required, and may be automatically controlled by a processing unit, a control unit or a computer device.

Table 2 shows a specific embodiment of an experimental flow chart of steps executed in the present disclosure, where the magnetic particles used in this experiment are magnetic ferric oxide nanoparticles, the magnetic particles have an average particle size of 180 nm and a ferric oxide concentration of 1.59 μg/μL, the amount of the magnetic particles used in the detection chamber is 100 μg, and a detection antibody is diluted to a concentration of 0.5 ng/μL. Table 2 shows various detailed parameters used in the steps such as working fluids, rotation rate of the cartridge, revolutions of the cartridge, waiting time, number of times of movement of the second magnetic unit, mixing time of the magnetic particles, rotation rate for discharging, revolutions for discharging and discharging time.

TABLE 2

Experimental flowchart of steps executed by the immunoassay centrifugal cartridge of the present disclosure

| No. | Working fluid (μL) | Rotation rate of cartridge (revolutions/minute) | Revolutions of cartridge | Waiting time (second) | Number of times of movement of second magnetic unit | Mixing time of magnetic particles (minute) | Rotation rate for discharging (revolutions/minute) | Revolutions for discharging | Discharging time (second) |
|---|---|---|---|---|---|---|---|---|---|
| 1 | IO beads-63 | 2000 | 100 | 3 | 0 | 0 | 2000 | 1000 | 30 |
| 2 | Lysis samples-62 | 2000 | 100 | 3 | 30 | 10 | 2000 | 1000 | 30 |
| 3 | Wash-62 | 2000 | 100 | 3 | 20 | 2 | 2000 | 1000 | 30 |
| 4 | Wash-62 | 2000 | 100 | 3 | 20 | 2 | 2000 | 1000 | 30 |
| 5 | Ab-62 | 2000 | 100 | 3 | 20 | 2 | 2000 | 1000 | 30 |
| 6 | Wash-62 | 2000 | 100 | 3 | 20 | 2 | 2000 | 1000 | 30 |
| 7 | Wash-62 | 2000 | 100 | 3 | 20 | 2 | 2000 | 1000 | 30 |
| 8 | TMB-62 | 2000 | 100 | 3 | 5 | 0.5 | 0 | 0 | 0 | magnetic unit 60. After reaction is finished, the cartridge 10 is driven to rotate, so that the working fluid is discharged into the waste chamber 46 through the capillary U-shaped guiding groove 434 and then discharged out of the cartridge 10 by the centrifugal force. Meanwhile, the third gas exhaust passage 446 (shown in FIG. 5) may ensure that during discharging of the working fluid, the working fluid can be discharged to the waste chamber 46. During discharging, since the magnetic particles 47 are drawn by the magnetic force of the first magnetic unit 60, the magnetic particles 47 will not be discharged along with the working fluid. The above steps may be repeated to introduce different working fluids into the detection chamber 45 in sequence, and the magnetic particles 47 may be mixed with and react with the different working fluids in sequence. Sizes of geometrical structures of sectional areas of the fluid chamber 41, the pin chamber 42, the second microchannel 432A, the buffer chamber 44, the third microchannel 433, the detection chamber 45, the capillary U-shaped guiding groove 434 and the waste chamber 46 may be designed as required, so as to regulate a pressure required for filling the working fluid. The smaller the size is, the larger the pressure difference required for driving the fluid is, which easily forms the effect of a block valve; on the contrary, the larger the size is, the smaller the pressure difference required for driving the working fluid, allowing the fluid to flow more easily. Rotation and stopping of the cartridge 10, the rotation rate of the cartridge 10, the pierced position of the pin-film assembly 50 and the rate and number of times of vertical reciprocating movement of the second magnetic unit 70 are Here, No. 1 to No. 8 represent a first fluid tank to an eighth fluid tank, each of the fluid tanks stores a required working fluid in a sealed manner, IO beads-63 μL represents a magnetic particle diluent, Lysis samples-62 μL is diluted blood, Ab-62 μL is a detection antibody diluent, TMB-62 μL represents a developing solution, and Wash-62 μL is a washing solution.

First, the pin-film assembly pierces the working fluid (IO beads-63 μL, magnetic particle diluent) of the first fluid tank, and the cartridge is rotated at 2000 rpm for 100 revolutions in 3 seconds, so that the working fluid of the first fluid tank is driven by the centrifugal force to flow into the detection chamber. By capillary action, a part of the magnetic particle diluent is gradually introduced into the capillary U-shaped guiding groove. After a waiting time of 30 seconds, the cartridge is driven to rotate again (2000 rpm, 1000 revolutions, and 30 seconds), so as to discharge the magnetic particle diluent (not containing any magnetic particle) into the waste chamber. During rotation, the magnetic particles inside the detection chamber are always drawn onto the side wall of the detection chamber by the fixed first magnetic unit, waiting for reaction with a next working fluid.

Then, the pin-film assembly pierces the working fluid (Lysis samples-62 μL, diluted blood) of the second fluid tank, and the cartridge is rotated at 2000 rpm for 100 revolutions in 3 seconds, so as to introduce the working fluid (Lysis samples-62 μL, diluted blood) of the second fluid tank into the detection chamber. The second magnetic unit is driven to move vertically in a reciprocating manner, for 30 times in 10 minutes, so that the magnetic particles are uniformly mixed in the working fluid (Lysis samples-62 μL, diluted blood). After reaction is finished, a discharging procedure is executed by the centrifugal force (2000 rpm, 1000 revolutions, and 30 seconds). Likewise, the magnetic particles are maintained inside the detection chamber during discharging.

Secondly, the pin-film assembly pierces the third to eighth fluid tanks in sequence, so that different working fluids shown in Table 2 flow into the detection chamber. The magnetic particles inside the detection chamber are driven to repeatedly move to-and-fro, so that the magnetic particles undergo reaction, washing and color reaction in sequence. Finally, the optical detection system interprets light transmission for the solution inside the detection chamber.

Figure 14:
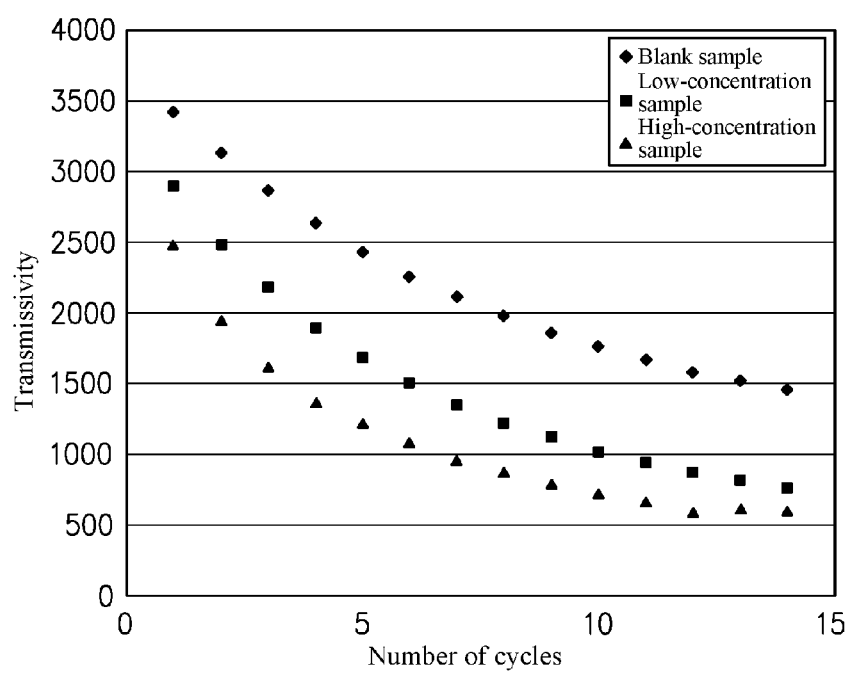
FIG. 14 is a statistical chart of results of immune response analysis according to an embodiment of the present disclosure.

According to the Beer-Lambert law, transmissivity $T=(I/I_o)$, and absorbance $A=-\log(I/I_o)=\epsilon*b*c$, where I is intensity of transmitted light, and $I_o$ is intensity of incident light. When a light ray is incident on a sample solution, a part of the light ray is absorbed by the sample solution, and the remaining part of the light ray is transmitted through the sample solution. When a parallel monochromatic light ray passes through a solution, absorbance (A) of the solution is in direct proportion to a product of multiplying molar absorptivity ($\epsilon$), optical path length (b) and solution concentration (c). The Beer-Lambert law is the basis of spectrophotometric quantitative analysis. After a blank sample, a high-concentration sample and a low-concentration sample undergo reaction at the cartridge, data collected by the optical detection system is as shown in FIG. 14, and a relationship between the sample concentration (c) in the solution and the measured transmissivity (T) is $c=k*(-\log T)$, where k is an arbitrary constant. The high-concentration sample has low transmissivity; the low-concentration sample has high transmissivity, and as the number of cycles increases, the value of transmissivity (T) decreases gradually, proving that the present disclosure surely can be implemented. The blank sample represents a control group, and the low-concentration sample and the high-concentration sample respectively represent experimental groups with normal and abnormal clinical glycated hemoglobin levels, with implementation results shown in FIG. 14.

Based on the above, the immunoassay test apparatus provided in the present disclosure relates to a flow path structure, a magnetic particle mixing mechanism and a pore apparatus related to immunoassay, a flow path structure driven by a centrifugal force and a capillary force, a system for sequentially performing centrifugal quantization, magnetic particle mixing, discharging and analysis for a specimen or tested working fluid, and a method and a flow path structure thereof, and which may be used as a carrier for immunological or biochemical test. Particularly, through a magnetic unit attraction step and a magnetic particle mixing step, an antibody on the magnetic particle can be sequentially bound to an antigen of the working fluid, bound to an enzyme-labeled detection antibody, and finally mixed with an enzyme-substrate hydrolysis developing solution for color reaction.

In the present disclosure, a sequence of working fluids is sealed in the cartridge in advanced, and then delivered to a user, who performs a film piercing operation through the pin-film assembly, so that the working fluids flow into the detection chamber. Next, the magnetic particles are mixed and react with different working fluids, thereby achieving quantitative color reaction for the specimen. In the present disclosure, through proper cooperation of the microchannel structure, the centrifugal force, the fixed first magnetic unit and the movable second magnetic unit, the magnetic particles will not be carried away by the working fluid during discharging, but are maintained on the side wall of the detection chamber. After another working fluid is driven by the centrifugal force to the detection chamber, the movable magnetic unit is moved towards and away from the detection chamber to cooperate with the fixed magnetic unit, to draw and move the magnetic particles between two side walls, so as to mix the magnetic particles with the working fluids, thereby improving the test yield.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An immunoassay test apparatus, comprising:
   a cartridge, capable of rotating about a reference axis, and having at least one test unit, wherein the test unit comprises:
   a plurality of fluid chambers, wherein each of the fluid chambers stores a working fluid,
   a plurality of pin chambers, wherein each of the pin chambers is corresponding to one of the fluid chambers, each of the pin chambers is configured with a first sealing film, and the first sealing film is used for preventing the pin chamber from communicating with the fluid chamber,
   a microchannel structure, communicating each of the pin chambers, wherein the microchannel structure is used for guiding the working fluid to flow from the fluid chamber to a detection chamber,
   a buffer chamber, connected to the microchannel structure,
   the detection chamber, in communication with the buffer chamber,
   a waste chamber, in communication with the detection chamber,
   a capillary U-shaped guiding groove, connecting the detection chamber and the waste chamber, and
   a gas exhaust structure, connected to the buffer chamber and the plurality of fluid chambers;
   a pin-film assembly, comprising:
   a second sealing film, disposed on and covering one surface of the cartridge where the detection chamber is disposed,
   a plurality of pierce mechanisms, disposed on the second sealing film, wherein each of the pierce mechanisms is corresponding to one of the pin chambers, each of the pierce mechanisms comprises a pin and a flexible structure, and the flexible structure is arranged for allowing the pin to move from a first position to a second position, and
   a first actuation unit, for driving the pin to move from the first position to the second position, wherein upon moving from the first position to the second position, the pin pierces the first sealing film, so that the pin chamber is in communication with the fluid chamber;
   a plurality of magnetic particles, disposed inside the detection chamber, wherein each of the magnetic particles is capable of magnetic attraction, and each of the magnetic particles has a first marked substance on a surface thereof;
   at least one first magnetic unit, disposed on one side of the detection chamber, wherein the first magnetic unit is used for producing a magnetic field on the plurality of magnetic particles, so as to draw and attach the plurality of magnetic particles to the side of the detection chamber where the first magnetic unit is disposed; and
   at least one second magnetic unit, capable of moving reciprocatingly between a third position and a fourth position, wherein a magnetic force of the second magnetic unit is larger than that of the first magnetic unit, and when the second magnetic unit is located at the fourth position, the second magnetic unit is located on one side of the detection chamber opposite to the first magnetic unit, and the second magnetic unit produces a magnetic field on the plurality of magnetic particles, so as to draw and attach the plurality of magnetic particles to the side of the detection chamber where the second magnetic unit is disposed.

2. The immunoassay test apparatus according to claim 1, wherein the flexible structure is a conical cylindrical structure, the flexible structure has a first end and a second end opposite to each other in an axial direction thereof, the first end has an outer diameter larger than that of the second end, a pore is formed in the second sealing film at a position corresponding to each of the pin chambers, the first end of the flexible structure is connected to the pore, the second end of the flexible structure protrudes from a surface of the second sealing film opposite to the cartridge, the pin has two opposite ends, one end of the pin is connected to the second end of the flexible structure, and an other end of the pin faces the cartridge.

3. The immunoassay test apparatus according to claim 2, wherein the end of the pin facing the cartridge is a tapered structure, at least one guide slot is formed in a surface of the tapered structure, and the guide slot extends for a length in an axial direction of the pin.

4. The immunoassay test apparatus according to claim 1, wherein the first actuation unit comprises:
   a push rod, wherein an axial end of the push rod faces the pierce mechanism; and
   a first actuator, for driving the push rod to move axially, so that the push rod moves relative to the pierce mechanism.

5. The immunoassay test apparatus according to claim 1, further comprising a tray, for holding the cartridge, wherein a connection structure is disposed between the tray and the cartridge, so that the tray and the cartridge are capable of rotating synchronously.

6. The immunoassay test apparatus according to claim 5, wherein the first magnetic unit is configured to protrude from a surface of the tray where the cartridge is disposed, a first recess is formed in the cartridge at a position corresponding to the first magnetic unit, and the first magnetic unit is embedded in the first recess.

7. The immunoassay test apparatus according to claim 5, wherein a through hole is formed in the tray at a position corresponding to the second magnetic unit, a second recess is formed in the cartridge at a position corresponding to the second magnetic unit, the second magnetic unit is disposed on a surface of the tray opposite to the cartridge, and when the second magnetic unit is located at the fourth position, the second magnetic unit extends through the through hole and is located inside the second recess.

8. The immunoassay test apparatus according to claim 5, further comprising at least one support frame structure, wherein the support frame structure comprises:
   a base;
   a test platform, for holding the tray;
   a plurality of support columns, disposed between the base and the test platform, wherein the plurality of support columns is used for supporting the test platform;
   a plurality of guide rods, disposed on a surface of the test platform where the tray is disposed; and
   a darkroom structure, disposed on the surface of the test platform where the tray is disposed, wherein the darkroom structure is connected to the plurality of guide rods, the darkroom structure is capable of moving reciprocatingly in an axial direction of the guide rod, and the darkroom structure is used for covering the cartridge.

9. The immunoassay test apparatus according to claim 8, wherein the support frame structure further comprises at least one fixed bracket, the fixed bracket is configured with a second actuator, the second actuator is connected to the second magnetic unit, and the second actuator is used for driving the second magnetic unit to move reciprocatingly between the third position and the fourth position.

10. The immunoassay test apparatus according to claim 1, wherein the microchannel structure comprises:
    a first microchannel, having a radian, wherein a center of a circle of the radian is disposed eccentric to the reference axis; and
    a plurality of second microchannels, wherein each of the second microchannels extends radially about the reference axis, each of the second microchannels has two opposite ends, one end of each of the second microchannels is connected to the first microchannel, and an other end of each of the second microchannels is connected to one of the pin chambers.

11. The immunoassay test apparatus according to claim 10, wherein the first microchannel has a first end and a second end opposite to each other, one of the second microchannels is disposed at the first end of the first microchannel, one of the second microchannels is disposed at the second end of the first microchannel, the plurality of second microchannels has a length gradually decreasing from the first end of the first microchannel to the second end of the first microchannel, and the buffer chamber is disposed at the first end of the first microchannel.

12. The immunoassay test apparatus according to claim 10, wherein the microchannel structure further comprises a third microchannel, the third microchannel extends radially about the reference axis, one end of the third microchannel is connected to the buffer chamber, and an other end of the third microchannel is connected to the detection chamber.

13. The immunoassay test apparatus according to claim 1, wherein the plurality of pin chambers is disposed centered on and around the reference axis.

14. The immunoassay test apparatus according to claim 1, wherein a first side wall is disposed on one side of the detection chamber adjacent to the first magnetic unit, a second side wall is disposed on one side of the detection chamber adjacent to the second magnetic unit, and the first side wall and the second side wall are planes.

15. The immunoassay test apparatus according to claim 1, wherein the capillary U-shaped guiding groove comprises a first arc-shaped groove, a second arc-shaped groove, a first connection groove and a second connection groove, the first arc-shaped groove, the first connection groove, the second arc-shaped groove and the second connection groove are connected in series to form a U-shaped structure, one end of the first arc-shaped groove is connected to the detection chamber, and one end of the second connection groove is connected to the waste chamber.

16. The immunoassay test apparatus according to claim 15, wherein the second arc-shaped groove has a convex arc surface, the convex arc surface faces the reference axis, and a distance from the convex arc surface to the reference axis is smaller than that from the buffer chamber to the reference axis.

17. The immunoassay test apparatus according to claim 1, wherein the gas exhaust structure is connected to each of the fluid chambers, the waste chamber and the buffer chamber.

* * * * *